United States Patent
Koh et al.

(10) Patent No.: US 11,690,650 B2
(45) Date of Patent: Jul. 4, 2023

(54) APPARATUS FOR EXTRACTION OF AT LEAST ONE ELEMENT FROM A CAVITY AND A PRESSURE LIMITATION APPARATUS

(71) Applicant: MATERNAL NEWBORN HEALTH INNOVATIONS, PBC, Kinnelon, NJ (US)

(72) Inventors: Chong Yong Koh, Singapore (SG); Kiat Jin Cheng, Singapore (SG)

(73) Assignee: MATERNAL NEWBORN HEALTH INNOVATIONS, PBC, Parsippany, NJ (US)

( * ) Notice: Subject to any disclaimer, the term of this patent is extended or adjusted under 35 U.S.C. 154(b) by 161 days.

(21) Appl. No.: 17/371,147

(22) Filed: Jul. 9, 2021

(65) Prior Publication Data
US 2021/0401464 A1   Dec. 30, 2021

Related U.S. Application Data

(63) Continuation of application No. 15/502,185, filed as application No. PCT/SG2014/000403 on Aug. 27, 2014, now Pat. No. 11,097,992.

(51) Int. Cl.
| | |
|---|---|
| *A61B 17/44* | (2006.01) |
| *C05G 3/80* | (2020.01) |
| *A61B 17/42* | (2006.01) |
| *C05B 7/00* | (2006.01) |
| *C05F 3/00* | (2006.01) |

(Continued)

(52) U.S. Cl.
CPC ............ *A61B 17/442* (2013.01); *A61B 17/42* (2013.01); *C05B 7/00* (2013.01); *C05F 3/00* (2013.01);
(Continued)

(58) Field of Classification Search
CPC .................. A61B 17/42; A61B 17/442; A61B 2017/00557; A61B 2017/445;
(Continued)

(56) References Cited

U.S. PATENT DOCUMENTS

| | | | | |
|---|---|---|---|---|
| 4,102,342 A | * | 7/1978 | Akiyama | ........ A61M 25/10183 604/920 |
| 4,243,040 A | | 1/1981 | Beecher | |

(Continued)

FOREIGN PATENT DOCUMENTS

| | | |
|---|---|---|
| CN | 101754721 A | 6/2010 |
| CN | 102343116 A | 2/2012 |

(Continued)

OTHER PUBLICATIONS

Chinese Office Action for application No. 201480081519.5 dated Jul. 19, 2019.
(Continued)

*Primary Examiner* — Jocelin C Tanner
(74) *Attorney, Agent, or Firm* — Botos Churchill IP Law LLP

(57) ABSTRACT

There is provided an apparatus for extraction of at least one object from a cavity. The apparatus includes a sleeve including an inflatable section configured to surround the at least one object during inflation; a handle configured to enable a user to hold the sleeve, the handle defining a holding edge of an opening at a first portion of the sleeve; and a handle-mount mounted to a peripheral area around the opening, the handle-mount being for attachment of a pump used for inflating the inflatable section. There is also provided a pressure limitation apparatus configured to operate with a birth assistance device when attached via a conduit.

1 Claim, 14 Drawing Sheets

(51) Int. Cl.
  *C05F 5/00* (2006.01)
  *C05F 9/04* (2006.01)
  *C05F 11/00* (2006.01)
  *C09K 17/48* (2006.01)
  *A61B 17/00* (2006.01)

(52) U.S. Cl.
  CPC ............... *C05F 5/004* (2013.01); *C05F 9/04* (2013.01); *C05F 11/00* (2013.01); *C05G 3/80* (2020.02); *C09K 17/48* (2013.01); *A61B 2017/00557* (2013.01); *A61B 2017/445* (2013.01); *A61B 2017/447* (2013.01)

(58) Field of Classification Search
  CPC . A61B 2017/447; A61B 11/0041; C05B 7/00; C05F 3/00; C05F 5/004; C05F 9/04; C05F 11/00; C05G 3/80; C09K 17/48; A61M 3/0262; A61M 3/0254; A61M 3/0233; A61M 25/1018; A61M 25/10181; A61M 25/10183; A61M 25/10185; A61M 25/10186
  See application file for complete search history.

(56) References Cited

U.S. PATENT DOCUMENTS

| | | | |
|---|---|---|---|
| 4,488,853 A | 12/1984 | Benson | |
| 4,598,707 A * | 7/1986 | Agdanowski | A61M 16/04 604/920 |
| 5,395,379 A | 3/1995 | Deutchman et al. | |
| 6,074,399 A | 6/2000 | Wallace et al. | |
| 8,876,760 B2 | 11/2014 | Bosman et al. | |
| 9,247,958 B2 | 2/2016 | Odon | |
| 10,238,423 B2 | 3/2019 | Odon | |
| 2004/0111050 A1 | 6/2004 | Smedley et al. | |
| 2010/0241134 A1* | 9/2010 | Odon | A61B 17/42 606/123 |
| 2011/0160847 A1* | 6/2011 | Oepen | A61F 2/958 623/2.11 |
| 2012/0265171 A1 | 10/2012 | Thorne, Jr. | |
| 2013/0324793 A1 | 12/2013 | Derus et al. | |
| 2014/0046288 A1 | 2/2014 | Geipel | |

FOREIGN PATENT DOCUMENTS

| | | |
|---|---|---|
| CN | 103687556 A | 3/2014 |
| EP | 2716243 A1 | 4/2014 |
| WO | 20020088546 A1 | 11/2002 |
| WO | 20160032394 A1 | 3/2016 |

OTHER PUBLICATIONS

Foreign Communication from a related counterpart application, ISR and Written Opinion dated Apr. 28, 2015, International Application No. PCT/SG2014/000403 filed Aug. 27, 2014.

Office Action issued in corresponding Indian Patent Application No. 201747007501 dated Aug. 13, 2020.

* cited by examiner

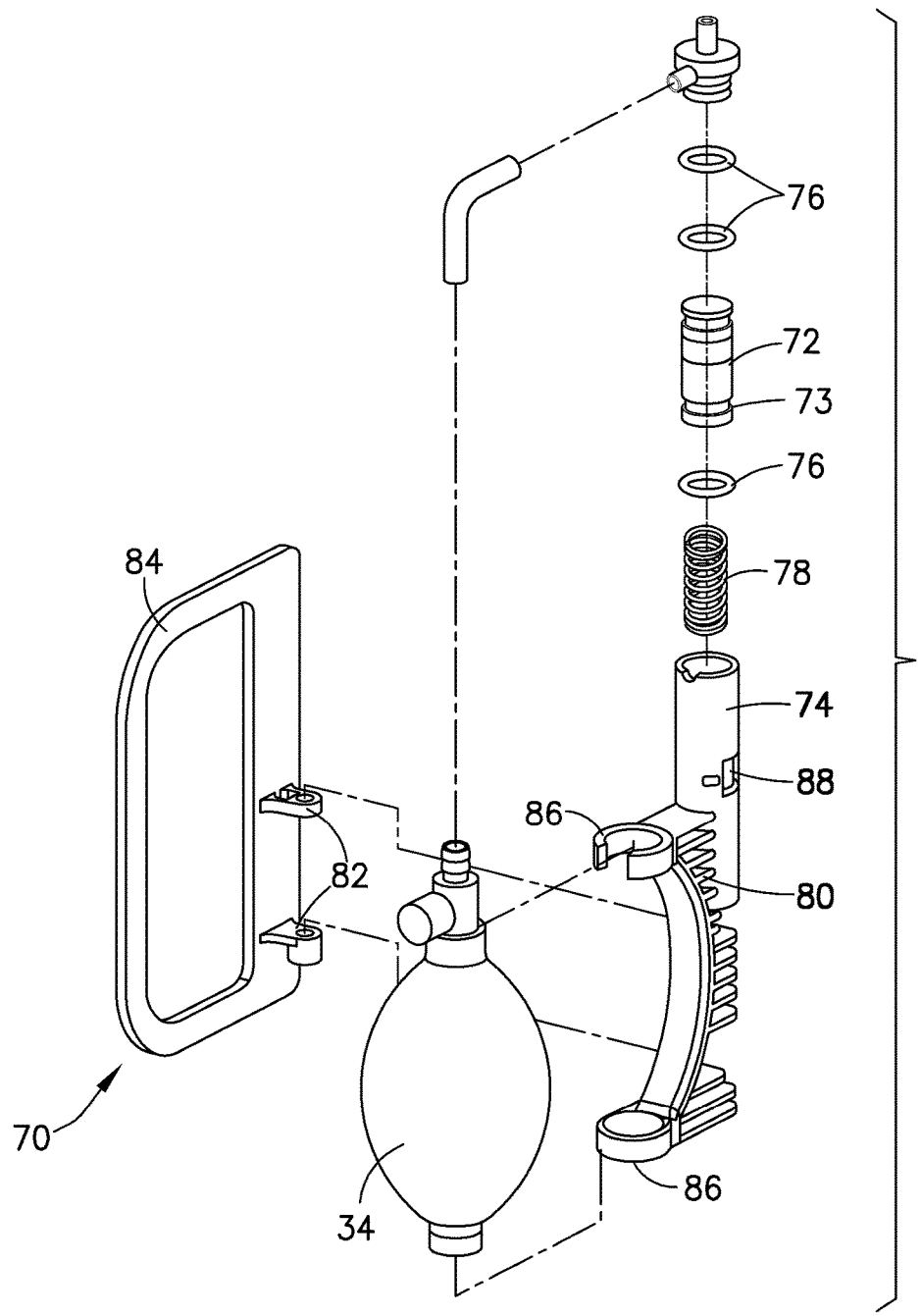

APPARATUS FOR EXTRACTION OF AT LEAST ONE ELEMENT FROM A CAVITY AND A PRESSURE LIMITATION APPARATUS

CROSS-REFERENCE TO RELATED APPLICATIONS

This application is a continuation of U.S. application Ser. No. 15/502,185, filed on Feb. 6, 2017, allowed, which application is a filing under 35 U.S.C. 371 as the National Stage of International Application No. PCT/SG2014/000403, filed Aug. 27, 2014, entitled "AN APPARATUS FOR EXTRACTION OF AT LEAST ONE ELEMENT FROM A CAVITY AND A PRESSURE LIMITATION APPARATUS," which is incorporated herein by reference in its entirety for all purposes.

FIELD OF THE INVENTION

The invention relates to an apparatus for extraction of at least one element from a cavity, specifically, in the instance of child birth, and also generally relates to an apparatus for limiting applied pressure.

BACKGROUND OF THE INVENTION

There have been several innovations in the field of child birth which aid in the child bearing process even in situations when healthcare professionals/facilities are not available. Some of these innovations are related to minimising potentially fatal maternal complications (for example, haemorrhages, infection) and newborn complications (for example, birth asphyxia, trauma) during the second stage of labour.

One example of such an innovation is the Odon device which is shown in FIG. 1. The device can be broadly described as an instrument to deliver a foetus when complications occur during the second stage of labour. The device includes a sleeve with an inflatable section made of film-like polyethylene material and operates in a different manner to a forceps and vacuum extractor for assisted deliveries. The device also provides an alternative to Caesarean delivery in situations when healthcare professionals/facilities are not available.

In addition, the apparatus for inflating the inflatable section currently does not have any manner of restricting the amount of air which enters the inflatable section. In some instances, it would be desirable to limit the air pressure in the inflatable section.

The present invention aims to enhance the Odon device.

SUMMARY OF THE INVENTION

There is provided an apparatus for extraction of at least one object from a cavity. The apparatus includes a sleeve including an inflatable section configured to surround the at least one object during inflation; a handle configured to enable a user to hold the sleeve, the handle defining a holding edge of an opening at a first portion of the sleeve; and a handle-mount mounted to a peripheral area around the opening, the handle-mount being for attachment of a pump used for inflating the inflatable section.

It is preferable that the handle-mount includes either a pump mounting with a grip mechanism or a pump stand with a grip mechanism.

It is advantageous that the handle-mount includes a hinge at a mid-portion of a frame of the handle-mount. The handle mount may include a viewing window, the viewing window being for providing an indication of pressure in the inflatable section. The handle mount can also include a main chamber; a piston configured to move within the main chamber; and a compression spring.

It is preferable that a body of the piston includes one of, for example, at least two coloured bands, numerical indicia, graduated markings and so forth.

The apparatus may further include a pump, the pump having a central chamber with a first compressible portion and a second incompressible portion. The pump is either a bulb pump or an axial pump, and it is preferable that the first compressible portion and the second incompressible portion remain in fluid communication.

In another aspect, there is provided a pressure limitation apparatus configured to operate with a birth assistance device when attached via a conduit to supply a positive pressure to inflate an inflatable section of the birth assistance device. The apparatus includes a central chamber for containing a gas, the central chamber including a first compressible portion and a second incompressible portion. The pressure limitation apparatus can also be configured to operate with a birth assistance device when attached via a conduit to supply a negative pressure to withdraw air from within a suction cup of the birth assistance device.

The apparatus is either a bulb pump or an axial pump, and it is preferable that the first compressible portion and the second incompressible portion remain in fluid communication. The first compressible portion may be defined using either an internal partition or an external restrictor. The first compressible portion may be a first sub-chamber.

DESCRIPTION OF FIGURES

In order that the present invention may be fully understood and readily put into practical effect, there shall now be described by way of non-limitative example only preferred embodiments of the present invention, the description being with reference to the accompanying illustrative figures.

FIG. 3(a) shows an exploded view and FIG. 3(b) shows a cross-sectional view of the second improvement respectively to the Odon device.

DETAILED DESCRIPTION

The present invention provides various improvements for an apparatus for extraction of at least one element from a cavity. The improvements broadly relate to improving a grip on an inflatable portion of the apparatus, and managing pressure of the inflatable portion of the apparatus. Several embodiments of the various improvements will be described in the following paragraphs. Advantageously, the present invention ensures that extraction of a baby from a vagina of a female during the child-birth process involves fewer disruptions.

Figure 1:
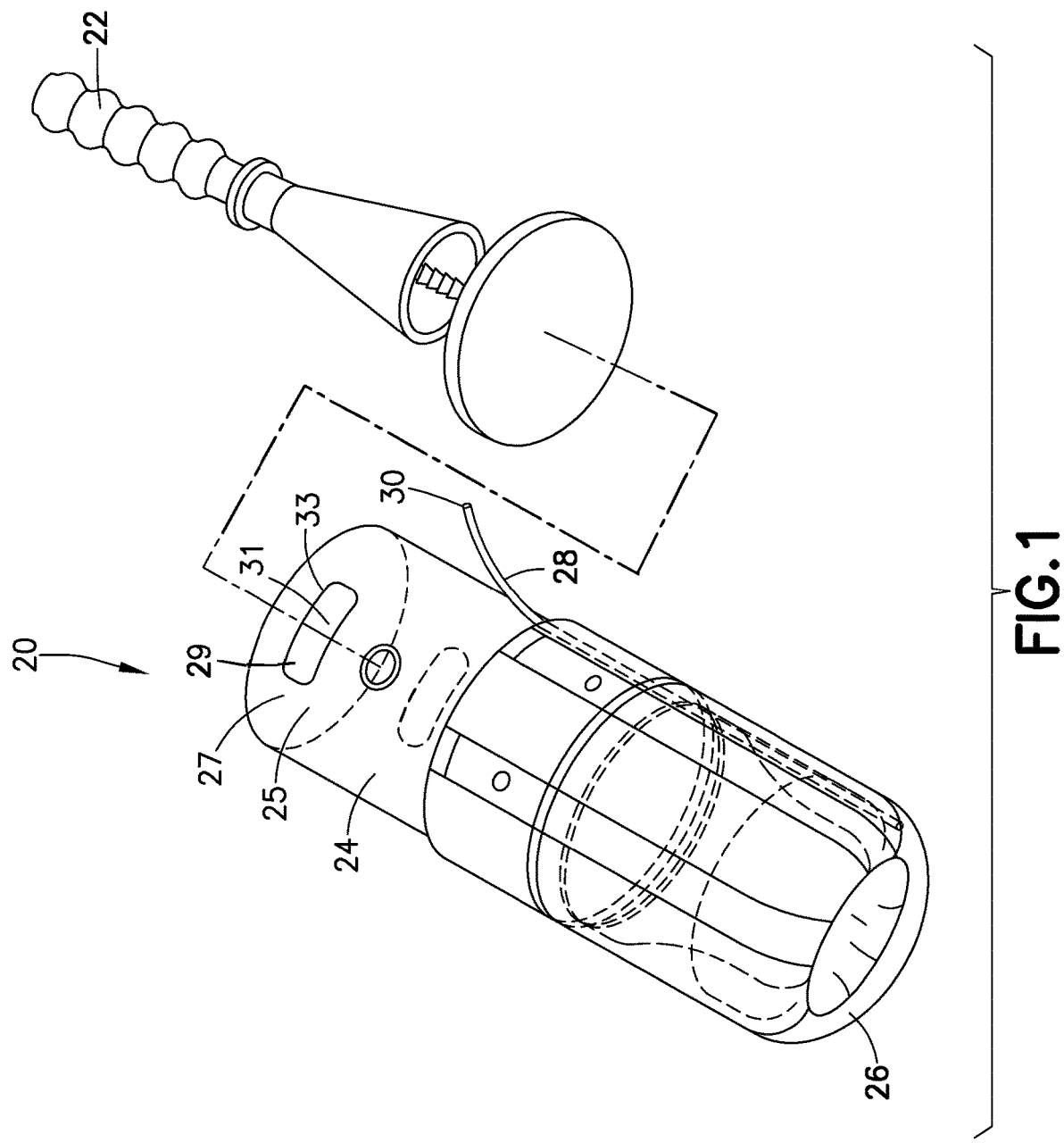
FIG. 1 shows a perspective view of various components of the Odon device.

Referring to FIG. 1, there is shown a perspective view of various components of an apparatus 20 (the Odon device) for extraction of at least one element from a cavity. Only main components of the apparatus 20 will be described, so as to enhance an understanding of the present invention. The apparatus 20 is for assisting the extraction of a baby from a vagina of a female during the child-birth process, and is used in certain situations when the female encounters difficulty during the child-birth process. The apparatus 20 includes a central inserter 22 which is removed after the apparatus 20 is appropriately positioned in the vagina of a female. The apparatus 20 also includes a sleeve 24. The sleeve 24 includes an inflatable section 26 configured to surround the at least one element during inflation, made of film-like polyethylene material. Ingress of air into the inflatable section 26 is via an inflation tube 28, and typically, a pump (not shown) is attached to the inflation tube 28 at a first end 30. The sleeve 24 also includes a handle 29 for a user to hold onto when removing the sleeve 24 from the vagina. The sleeve 24 includes an opening 31 at a first portion 25 of the sleeve 24, the opening 31 being configured to allow passage of the user's fingers when the user is holding onto the handle 29. The handle 29 defines a holding edge 33 of the opening 31.

Figure 2A:
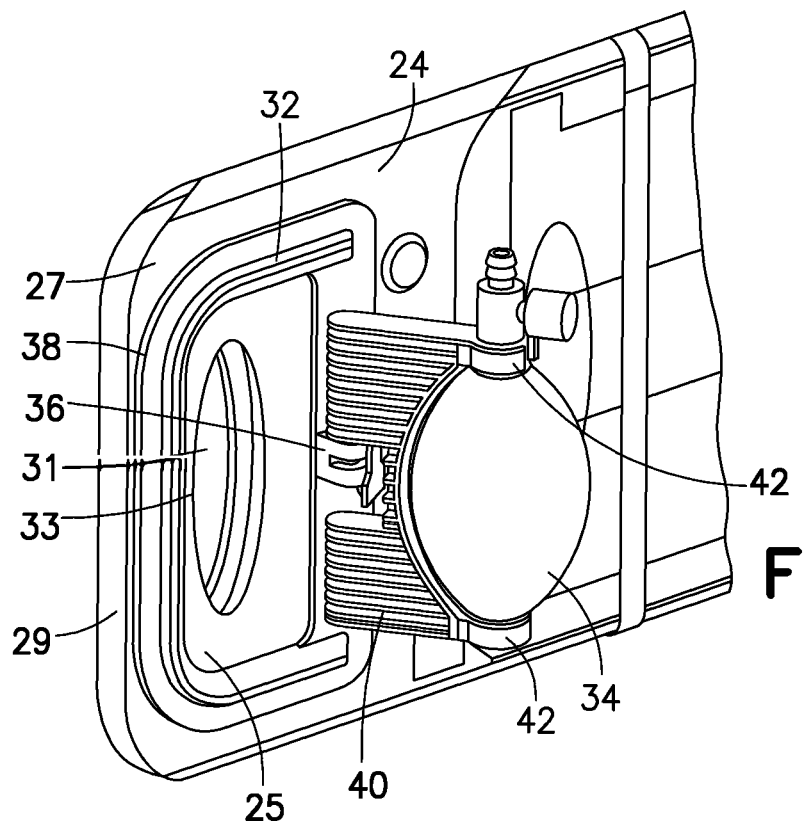
FIG. 2(a)-(b) show perspective views of two embodiments of a first improvement to the Odon device of FIG. 1.
Figure 2B:
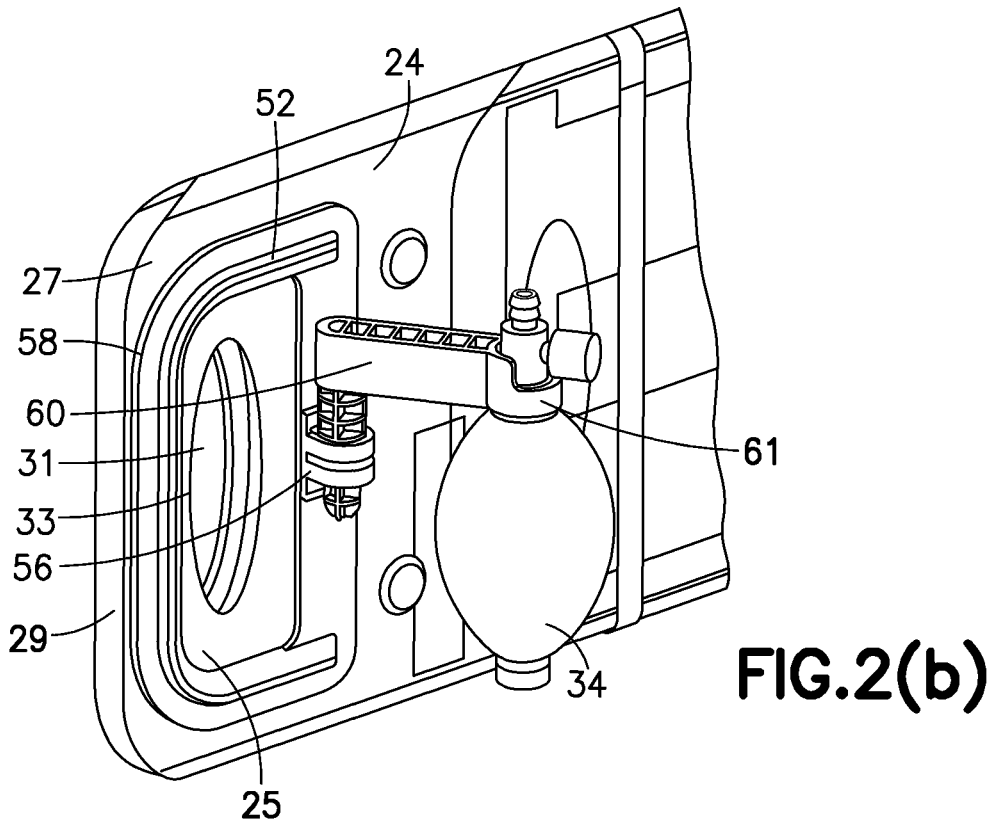

Referring to FIGS. 2(a) and 2(b), there are shown two embodiments incorporating a first improvement to the apparatus 20. The first improvement is a handle-mount 32/52 which is mounted to a peripheral area 27 around the opening 31 of the sleeve 24. The peripheral area 27 around the opening 31 can relate to a portion surrounding the opening 31, either partially along a perimeter of the opening 31 or along the entire perimeter of the opening 31. The handle-mount 32/52 is integral with the sleeve 24. The handle-mount 32/52 is fabricated from a plastics material like polyethylene and can be mounted to the sleeve 24 using, for example, heat sealing, adhesives, fasteners, snap-fit mounts, and so forth. The handle-mount 32/52 allows a pump 34 to be mounted to the sleeve 24 (whenever the pump 34 is coupled to the first end 30 of the inflation tube 28), and also provides rigidity to the handle 29 during use. Use of the handle-mount 32/52 frees up a hand of the user as the pump 34 is no longer dangling when coupled to the first end 30, and the free hand is able to apply pressure at an entrance of the vagina during removal of the sleeve 24 from the vagina. Furthermore, the additional rigidity of the handle 29 also provides a stiffer handle 29 when removing the sleeve 24 from the vagina. Moreover, the handle-mount 32/52 can also be used by both left-handed and right-handed users. The configurations shown in FIGS. 2(a) and 2(b) are for right-handed users. For the sake of clarity, the handle-mount 32/52 is mounted to another face of the sleeve 24 with the pump 34 in an inverted position (compared to the position of the pump 34 as shown in FIG. 2) for left-handed users.

The first embodiment of the handle-mount 32 is shown in FIG. 2(a). The handle-mount 32 includes a hinge 36 at a mid-portion of a frame 38 for a pump mounting 40. Having the hinge 36 at the mid-portion, rather than having top-bottom hinges, ensures that the pump mounting 40 does not deform during removal of the sleeve 24 from the vagina. The pump mounting 40 is shaped to receive the pump 34, the pump mounting 40 also including grip mechanisms 42 for end portions of the pump 34. The grip mechanism 42 can be a ring structure with an opening to allow placement of the pump 34.

The second embodiment of the handle-mount 52 is shown in FIG. 2(b). The handle-mount 52 includes a hinge 56 at a mid-portion of a frame 58 for a pump stand 60 to ensure that the pump stand 60 does not deform during removal of the sleeve 24 from the vagina. The pump stand 60 is shaped in a form of an elongated arm with a grip mechanism 61 to ensure optimal no-obstacle access to the pump 34 such that the user is able to have a wrap-around grip for the pump 34.

Referring to FIGS. 3 and 4, there is shown a second improvement of the apparatus 20. The second improvement is a pressure indicating handle mount 70. The pressure indicating handle mount 70 is also mounted to a peripheral area 27 around the handle 29 of the sleeve 24. The pressure indicating handle mount 70 is fabricated from a plastics material like polyethylene and can be mounted to the sleeve 24 using, for example, heat sealing, adhesives, fasteners, snap-fit mounts, and so forth. The pressure indicating handle mount 70 is able to provide a general indication of whether a pressure in the inflatable section 26 of the apparatus 20 is inadequate, sufficient or excessive.

Figure 3B:
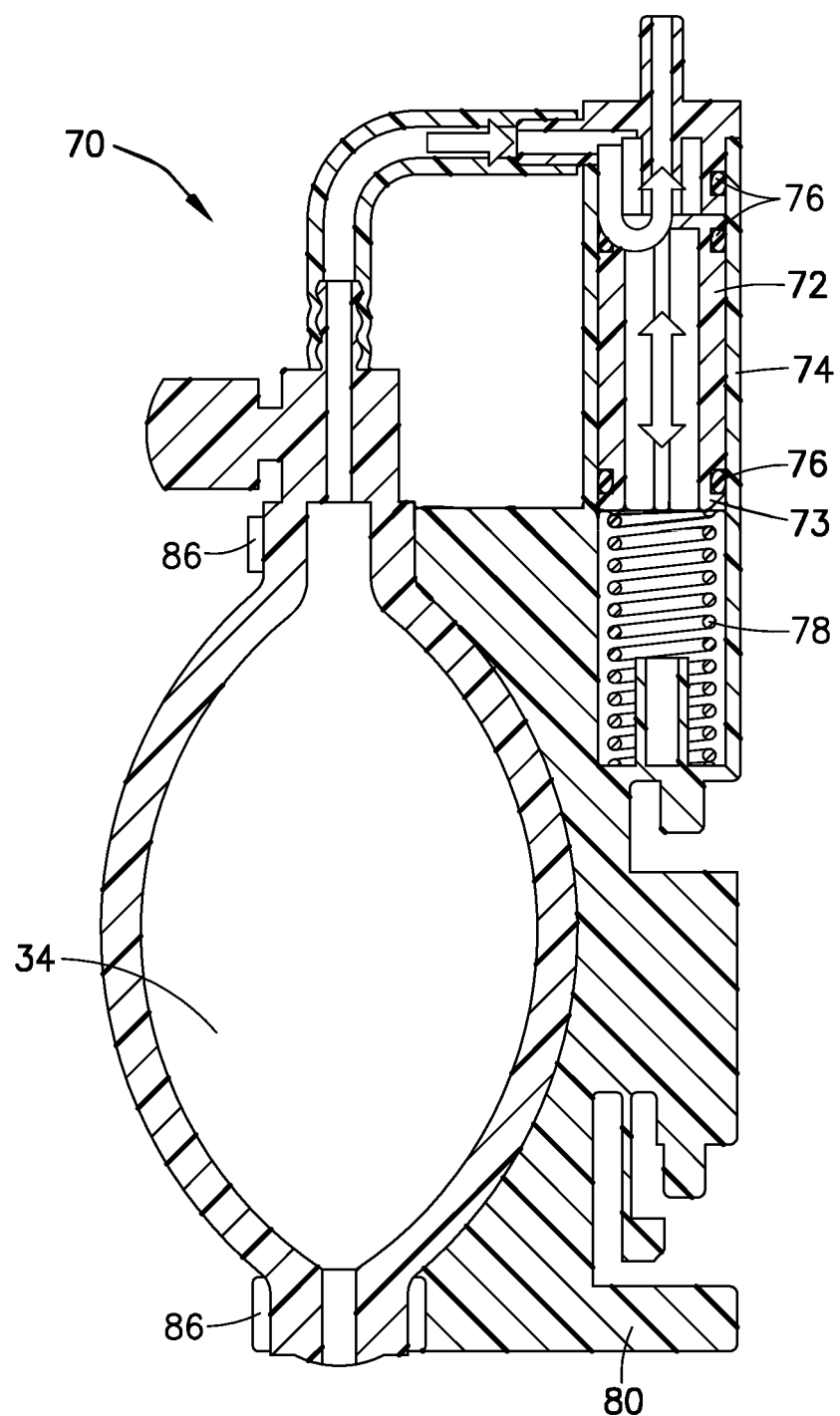

An exploded view of the pressure indicating handle mount 70 is shown in FIG. 3(a), while a cross-sectional view is shown in FIG. 3(b). The pressure indicating handle mount 70 includes a moving piston 72 which slides along a main chamber 74 in accordance with changes in pressure in the inflatable section 26. The pressure indicating handle mount 70 may include a plurality of o-rings 76 mounted to the moving piston 72 to provide a seal between the moving piston 72 and an inner surface of the main chamber 74. Alternatively, the moving piston 72 can be fitted in the main chamber 74 using an interference fit. In addition, the pressure indicating handle mount 70 also includes a compression spring 78 to provide a biasing force for the moving piston 72. The spring 78 provides a resistive force for the moving piston 72 as the pressure in the main chamber 74 is increased. A spring constant of the spring 78 can determine a movement of the moving piston 72 during pressurization of the main chamber 74, specifically pressurization at a lower portion 73 of the moving piston 72 and a wall of the main chamber 74. Furthermore, the pressure indicating handle mount 70 also includes a pump mounting 80 with two hinges 82 at a frame 84, whereby the pump mounting 80 is shaped to receive the pump 34, the pump mounting 80 also including attachment portions 86 for end portions of the pump 34. A body of the moving piston 72 can have at least two different coloured bands (for example, light, and dark) to indicate the pressure in the inflatable section 26 through a viewing window 88. It should be appreciated that a numerical representation of the pressure in the inflatable section 26 can also be shown through the viewing window 88 (particularly, calibration of the moving piston 72 of the pressure indicating handle mount 70 may be carried out). Furthermore, markings/graduations indicating the pressure in the inflatable section 26 can also be shown through the viewing window 88.

The moving piston 72 provides a seal to the main chamber 74 when pressure is built up in the main chamber 74, specifically pressurization at the lower portion 73 of the moving piston 72 and the wall of the main chamber 74. The plurality of o-rings 76 aids in providing a seal between the moving piston 72 and the inner surface of the main chamber 74 and also aids in maintaining stability of the moving piston 72 during motion.

Figure 4A:
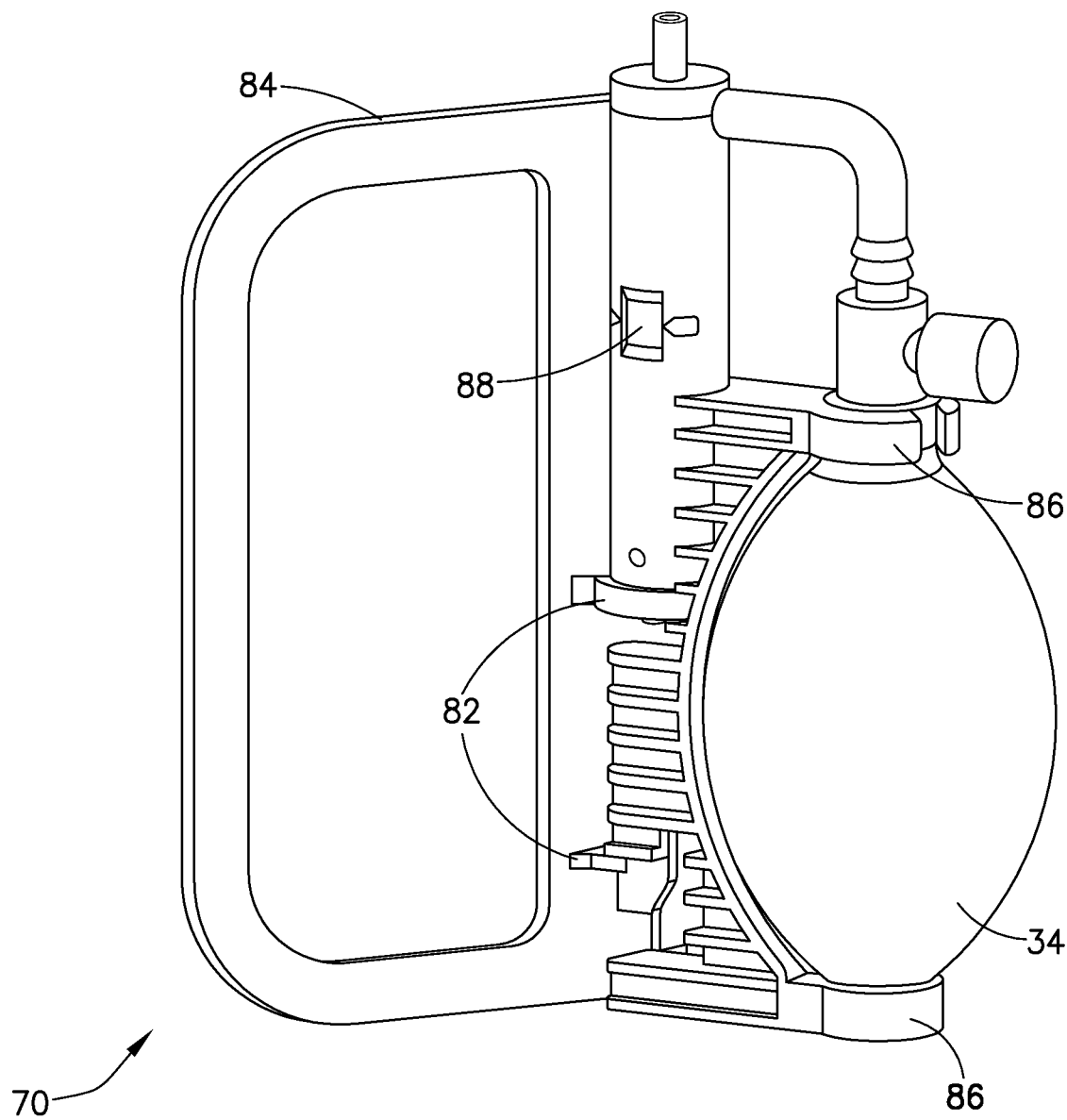
FIG. 4(a)-(c) shows the second improvement when in use.
Figure 4B:
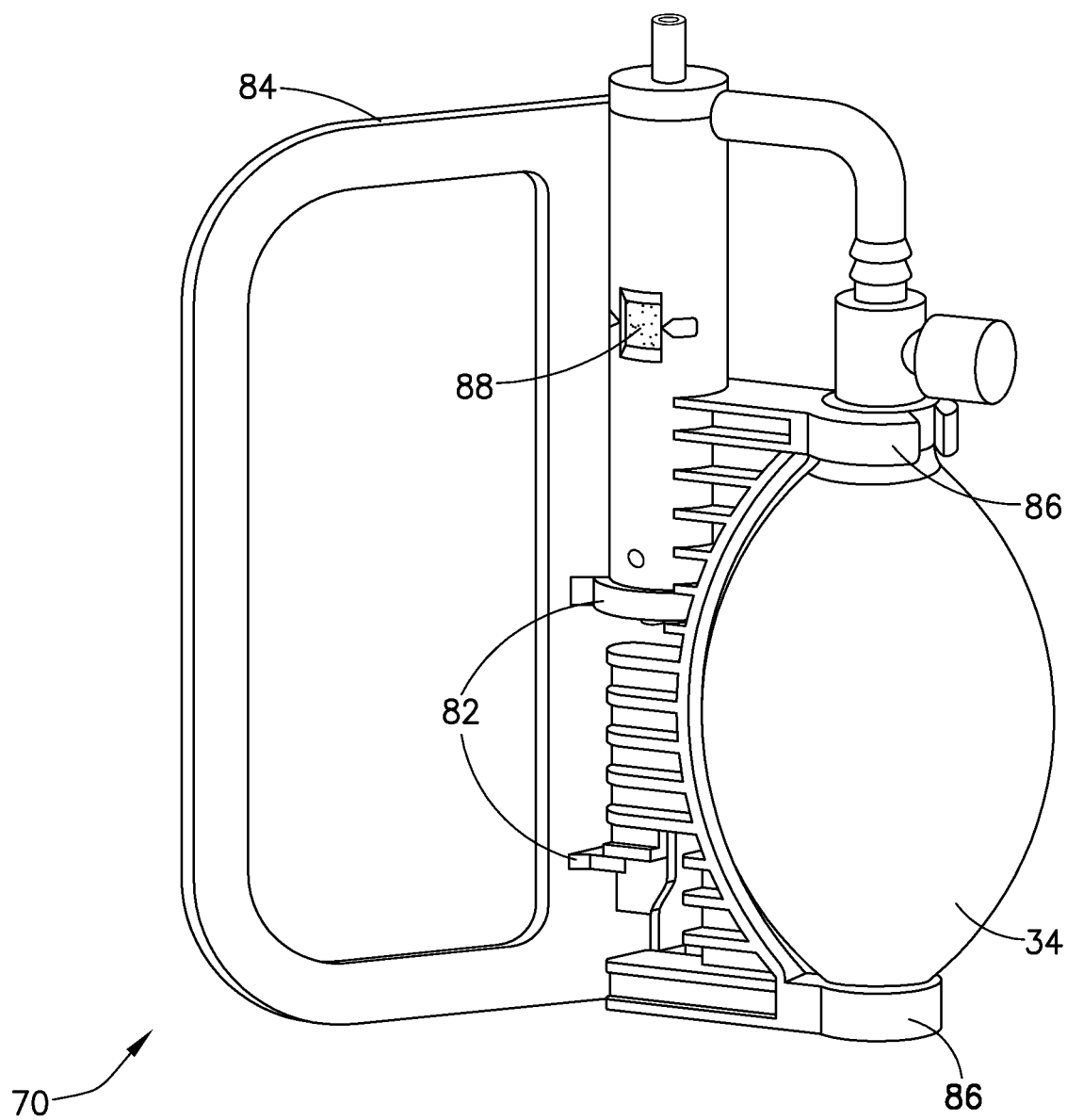
Figure 4C:
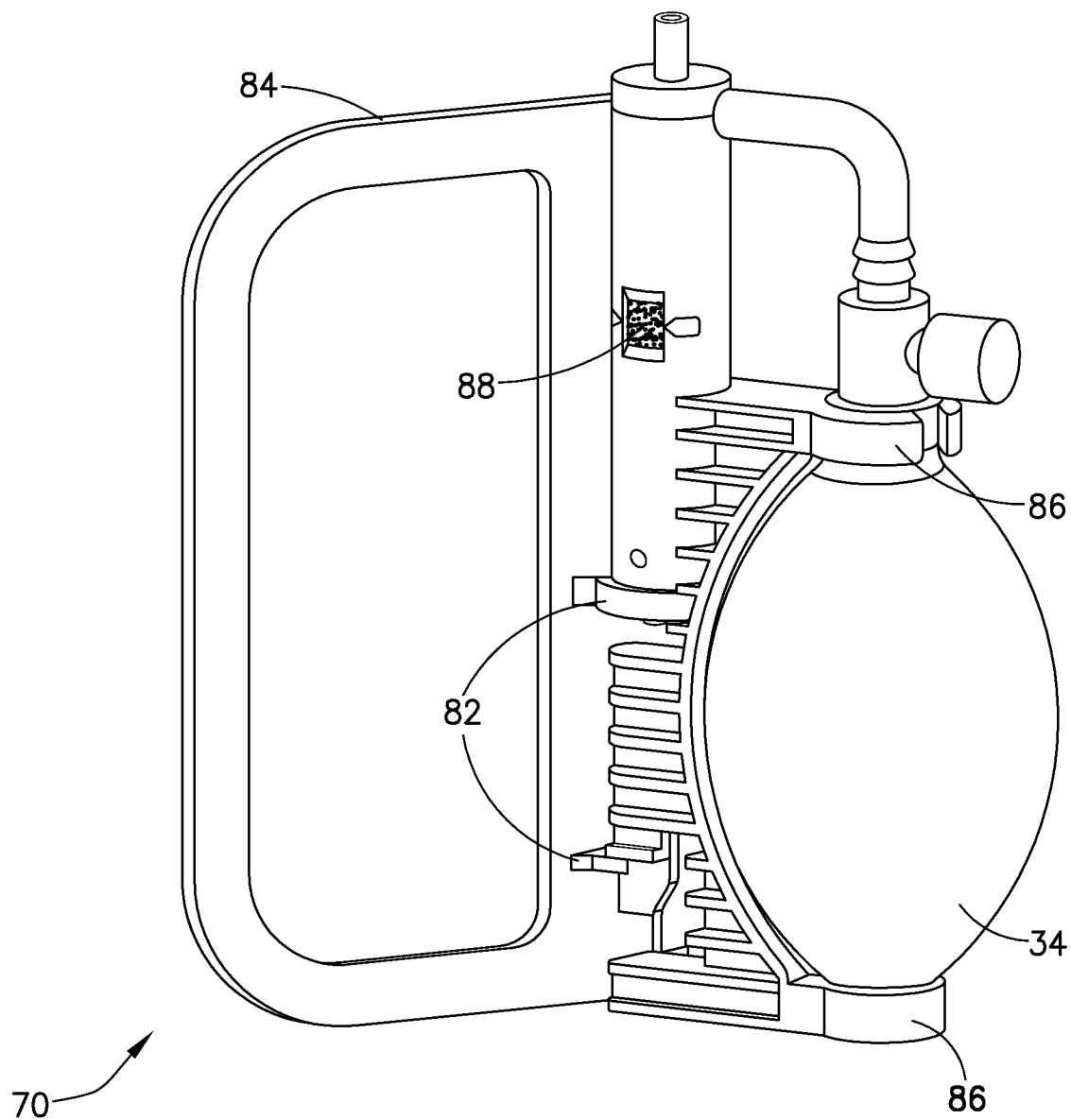

FIG. 4(a)-(c) shows the pressure indicating handle mount 70 during instances of use. FIG. 4(a) shows the pump 34 being compressed after the pump 34 has been connected to the pressure indicating handle mount 70. At this instance, a light coloured band of the moving piston 72 is indicated at the viewing window 88, and this indicates that pressure in the inflatable section 26 of the apparatus 20 is inadequate. FIG. 4(b) shows a darker coloured band of the moving piston 72 indicated at the viewing window 88 as the pump 34 is continually pumped from the state in FIG. 4(a), and this darker coloured band indicates that the pressure in the inflatable section 26 of the apparatus 20 is sufficient to provide adequate holding force during use of the apparatus 20. FIG. 4(*c*) shows a darkest coloured band of the moving piston 72 indicated at the viewing window 88 as the pump 34 is continually pumped from the state in FIG. 4(*b*), and this darkest coloured band indicates that the pressure in the inflatable section 26 of the apparatus 20 is excessive during use of the apparatus 20. The pressure indicating handle mount 70 ensures that the pressure in the inflatable section 26 can be monitored by the user such that it is at an optimal level during use of the apparatus 20.

Furthermore, it should be appreciated that similarities of the pressure indicating handle mount 70 and the handle-mount 32 mean that the pressure indicating handle mount 70 also provides the same advantages as the handle-mounted 32.

The following paragraphs provide theoretical aspects in relation to the workings of the pressure indicating handle mount 70.

Built-up pressure in the main chamber 74, $P_{pressure}$ chamber will push the moving piston 72 with Force, $F_{piston}$. The main chamber 74 has cross-sectional area, $A_{pressure\ chamber}$.

Given that Pressure=Force/Area, therefore $$P_{pressure\ chamber} = F_{piston}/A_{pressure\ chamber} \quad (1)$$

Where $A_{pressure\ chamber} = \pi(D/2)^2$
D=Pressure Chamber Diameter $$\text{Therefore, } F_{piston} = P_{pressure\ chamber} * A_{pressure\ chamber} \quad (2)$$

By selecting an appropriate spring constant, k, for the spring 78, the position of the moving piston 72 can be defined.

$$F_{spring} = k * \Delta x \quad (3)$$

$\Delta x$=Spring Compression=Position shift of Piston in relation to an original initial position Thus, assuming resistance of the spring force equals to force at moving piston 72, $$F_{spring} = F_{piston} \quad (4)$$

Substituting equations (2) and (3) into (4), $$k * \Delta x = P_{pressure\ chamber} * A_{pressure\ chamber}$$

$$\Delta x = [P_{pressure\ chamber} * A_{pressure\ chamber}]/k$$

Thus, as $A_{pressure\ chamber}$ and $P_{pressure\ chamber}$ can be defined based on product design and product requirement, by adjusting k, the position of the moving piston 72 can be defined.

Furthermore, assuming working pressure of apparatus 20 to be $P_{working}$, and excessive pressure to be $P_{exceed}$, the position of the moving piston 72 in relation to an original position are as shown below:

$$\Delta x_{working} = P_{working} * A_{pressure\ chamber}/k$$

$$\Delta x_{exceed} = P_{exceed} * A_{pressure\ chamber}/k$$

Where
$P_{working} < P_{exceed}$
$\Delta x_{working} < \Delta x_{exceed}$

Referring to FIGS. 5 to 7, there is shown a third improvement of the apparatus 20. The third improvement is a pressure limited pump 100. FIG. 5 shows schematic diagrams of the pressure limited pump 100 during use to supply positive pressure. It should be appreciated that the pressure limited pump 100 can be used with other birth assistance devices such as, for example, a ventouse. The pressure limited pump 100 is typically attached to the birth assistance device via a conduit. The pressure limited pump 100 can also be viewed as a pressure limitation apparatus. In addition, the pressure limited pump 100 is configured for operation involving gases.

FIG. 5(*a*) shows an initial state of the pressure limited pump 100 which includes a central chamber 99, a first check valve 102 and a second check valve 104. The central chamber 99 is for drawing air from atmosphere and expelling the air, and includes a compressible portion ($V_a$) and incompressible portion ($V_b$) which serves as pressure limit for the pressure limited pump 100. The first check valve 102 allows air to pass through when the central chamber 99 pressure ($P_{pump}$) is lower than atmospheric pressure ($P_0$). It also prevents back flow of air when air is being pressurized within the central chamber 99. The second check valve 104 allows air to pass through when $P_{pump}$ is higher than air chamber 106 pressure ($P_{air\ chamber}$). The air chamber 106 represents the inflatable section 26 of the sleeve 24. The second check valve 104 also prevents back flow of air from the air chamber 106 when air is being drawn from atmosphere into the central chamber 99. At the initial state, no air flow through the first check valve 102 and the second check valve 104. Thus, $q_1 = q_2 = 0$, and $P_{air\ chamber} = P_{pump} = P_0$.

FIG. 5(*b*) shows compression of the central chamber 99, leading to air passing through the second check valve 104 into the air chamber 106. At this juncture, $P_{pump} > P_{air\ chamber}$ and $q_2 > 0$. Subsequently, $P_{air\ chamber}$ increases due to displacement of air into the air chamber 106.

After FIG. 5(*b*), FIG. 5(*c*) shows the central chamber 99 drawing air from the atmosphere, thus increasing internal volume of the central chamber 99 and leading to air passing through the first check valve 102 into the central chamber 99. Thus, $P_{pump} < P_0$, $q_1 > 0$, $P_{pump} < P_{air\ chamber}$ and $q_2 = 0$.

When steps depicted in FIGS. 5(*b*) and 5(*c*) are repeated (that is, repeated pump-release actions on the central chamber 99), a juncture will be reached whereby pressure equilibrium is reached, that is $P_{pump} = P_{air\ chamber}$, and $q_1 = q_2 = 0$ since there is no air flow between any of the central chamber 99, the air chamber 106 and the atmosphere.

The following paragraphs provide theoretical aspects in relation to the workings of the pressure limited pump 100.

When pressure within the central chamber 99 ($P_{pump}$) is equal to the pressure of the air chamber ($P_{air\ chamber}$), no air will be transferred at the second check valve 104, as shown in FIG. 5(*d*).

Thus, by controlling a ratio of compressible volume (Va) and incompressible volume (Vb) in the central chamber 99, a maximum pressure that can be delivered by the central chamber 99 can be designed (defined) using Boyle's Law as follows:

$$\text{Boyle's Law: } P_1 V_1 = P_2 V_2 \quad (a)$$

$$\text{Initial Pressure: } P_1 = P_0 \quad (b)$$

$$\text{Initial Volume: } V_1 = V_a + V_b \quad (c)$$

Final Volume: $V_2 = V_b$ (that is, the incompressible volume) $\quad (d)$

Therefore, $$P_2 = P_1 \times V_1 / V_2 \quad \text{(e derived from equation a)}$$

Substitute (b), (c), (d) into (e);

$$P_2 = P_0 \times (V_a + V_b)/V_b$$

$P_2$=Final Pressure=Maximum Pressure Delivered=Pressure Limit

When, $P_{air\ chamber} = P_{pump} = P_2$
$q_2 = 0$

Therefore, by defining the ratio between the compressible volume, $V_a$, and incompressible volume, $V_b$, the maximum pressure delivered to the air chamber 106 can be limited. The pressure limited pump 100 ensures that the pressure in the inflatable section 26 is not excessive during use of the apparatus 20.

FIG. 6 shows various embodiments of the third improvement. FIGS. 6(a)-6(c) depict the central chamber 99 in a bulb pump configuration. FIG. 6(a) shows use of an internal partition (such as, for example, partitions, stoppers, membranes, and the like) within the central chamber 99 to define the compressible portion, $V_a$, and incompressible portion, $V_b$. FIG. 6(b) shows use of an external guide (restrictor) mounted to the central chamber 99 to define the compressible portion, $V_a$, and incompressible portion, $V_b$. FIG. 6(c) shows use of a separate compressible portion (a first sub-chamber), $V_a$, and a separate external incompressible portion (a second sub-chamber), $V_b$ to make up the central chamber 99.

Figure 6A:
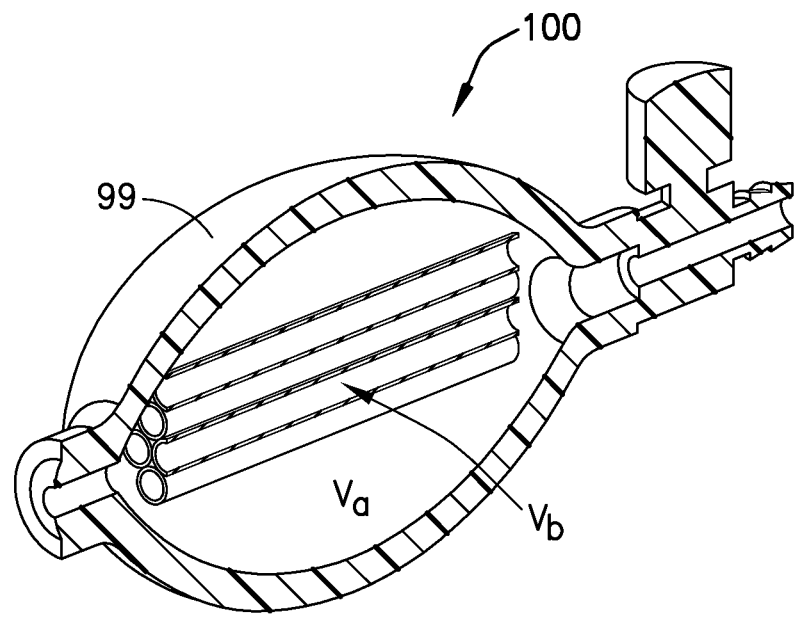
FIG. 6(a)-(f) show various embodiments of the third improvement.
Figure 6B:
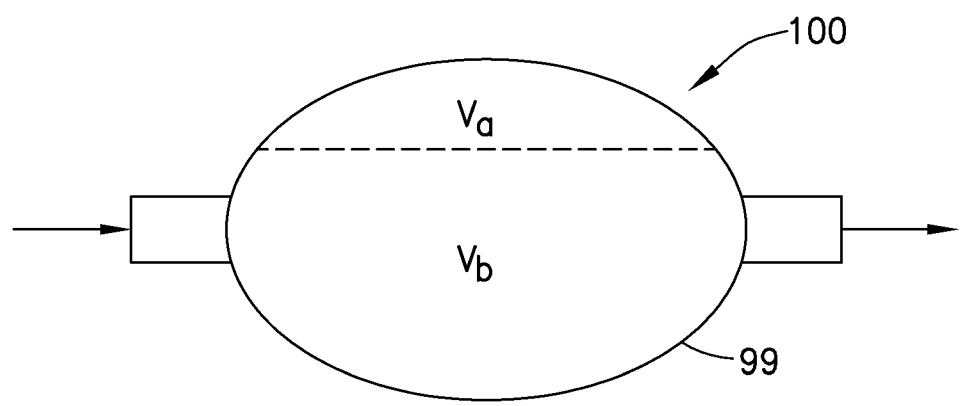
Figure 6C:
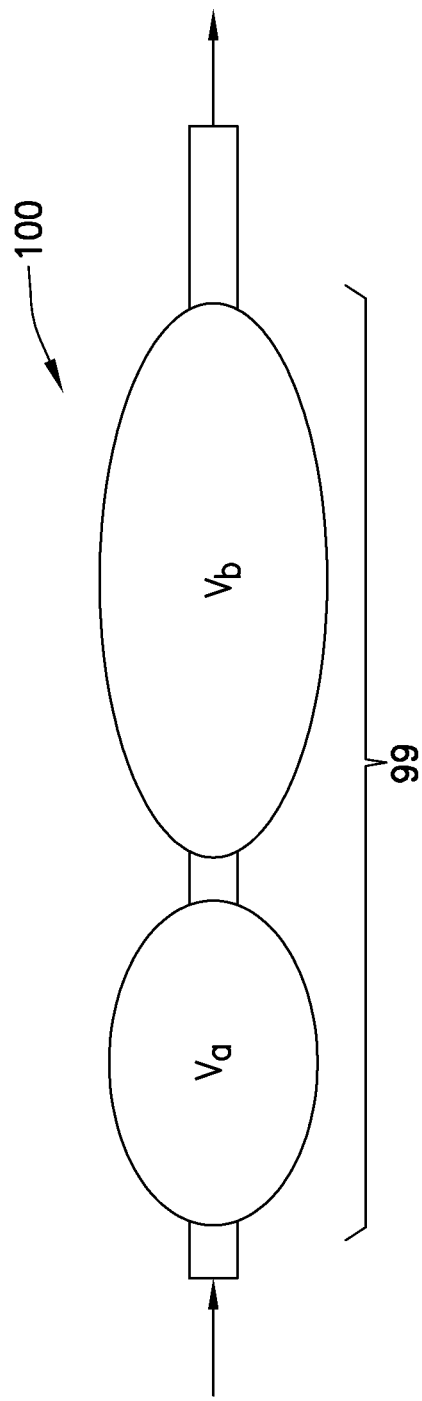
Figure 6D:
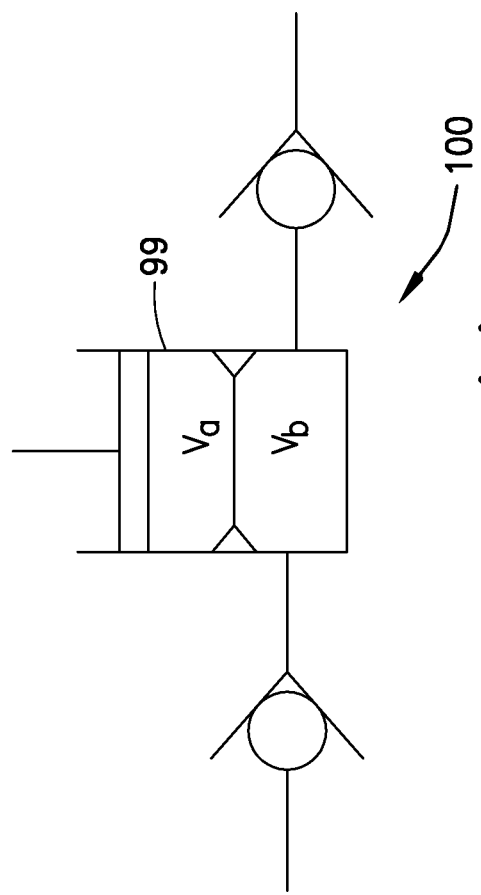
Figure 6E:
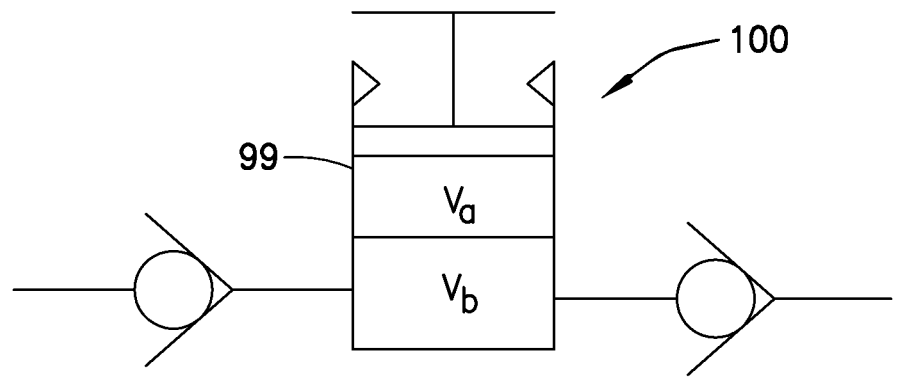
Figure 6F:
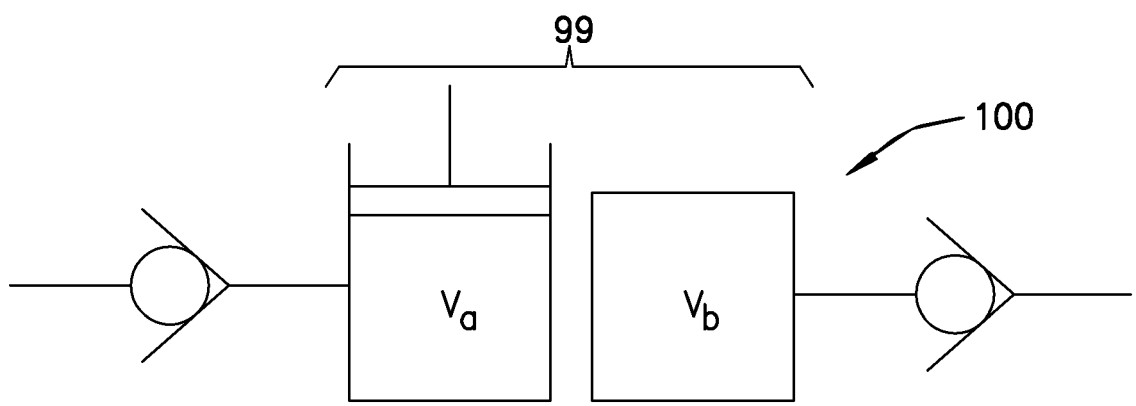

FIGS. 6(d)-6(f) depict the central chamber 99 in an axial pump configuration. FIG. 6(d) shows use of objects within the central chamber 99 to define the compressible portion, $V_a$, and incompressible portion, $V_b$. FIG. 6(e) shows use of an external guide (restrictor) mounted to the central chamber 99 to define the compressible portion, $V_a$, and incompressible portion, $V_b$. FIG. 6(f) shows use of a separate compressible portion, $V_a$, and a separate external incompressible portion, $V_b$ to make up the central chamber 99. It should be appreciated that other variations for the central chamber 99 are also possible. Moreover, it should be appreciated that in all the embodiments shown in FIG. 6, $V_a$ and $V_b$ remain in fluid communication.

It should be appreciated that the pressure limited pump 100 can be used to apply a positive pressure to supply air to an inflatable section 26 like that of the apparatus 20, and that it can also be used to apply a negative pressure to withdraw air from within an enclosed region (like a suction cup of a ventouse). It is critical to limit the negative pressure so as to minimize damage to a baby's head during delivery of the baby. Thus, the pressure limited pump 100 enables limitation of the negative pressure without the user's intervention, that is, without needing to monitor the pressure level within the enclosed region. Moreover, use of the pressure limited pump 100 results in redundancy of a pressure gauge and a pressure releaser which is typically used with the ventouse. Thus, a number of components which are required when using the ventouse is also minimized, correspondingly minimizing cost and device complexity.

Figure 7A:
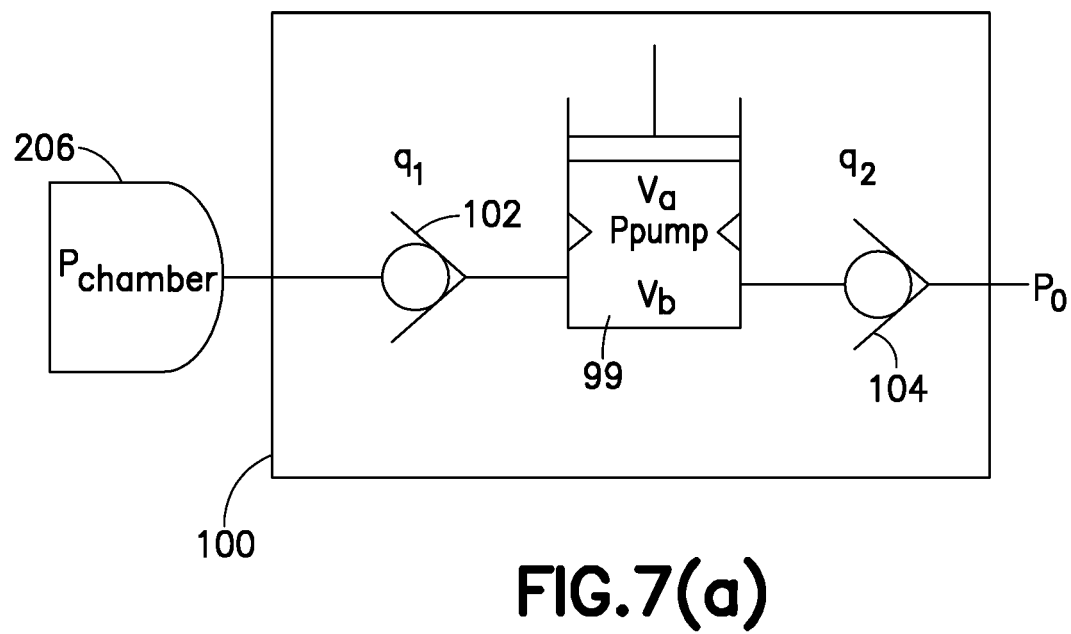
FIG. 7(a)-(c) show schematic diagrams of the third improvement during use when applying negative pressure.

In the instance when the pressure limited pump 100 is used to apply a negative pressure, referring to FIG. 7, FIG. 7(a) shows an initial state of the pressure limited pump 100 which includes a central chamber 99, a first check valve 102 and a second check valve 104. The central chamber 99 is a compressible portion ($V_a$) and incompressible portion ($V_b$) which serves as pressure limit for the pressure limited pump 100. The first check valve 102 allows air to pass through when the central chamber 99 pressure ($P_{pump}$) is higher than atmospheric pressure ($P_0$). It also prevents back flow of air when air is being pressurized within the central chamber 99. The second check valve 104 allows air to pass through when $P_{pump}$ is higher than air chamber 206 pressure (P chamber). The air chamber 206 represents the suction cup of the ventouse. At the initial state, no air flow through the first check valve 102 and the second check valve 104. Thus, $q_1=q_2=0$, and $P_{chamber}=P_{pump}=P_0$.

Figure 7B:
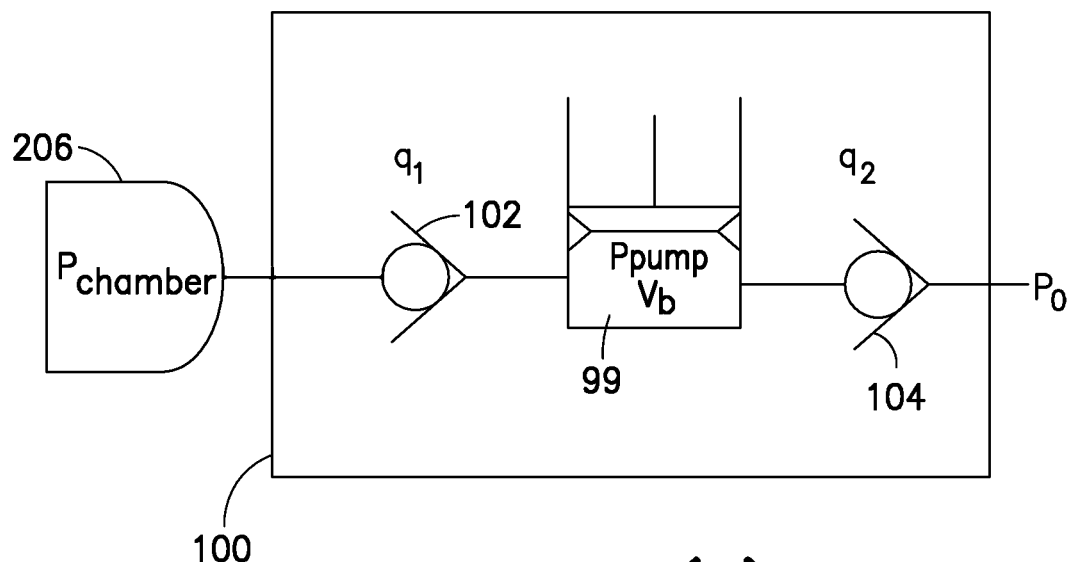

FIG. 7(b) shows compression of the central chamber 99, leading to air passing through the second check valve 104 into the atmosphere. At this juncture, $P_{pump}>P_0$.

After FIG. 7(a), FIG. 7(b) shows the central chamber 99 drawing air from the air chamber 206, thus increasing internal volume of the central chamber 99 and leading to air passing through the first check valve 102 into the central chamber 99.

Figure 5A:
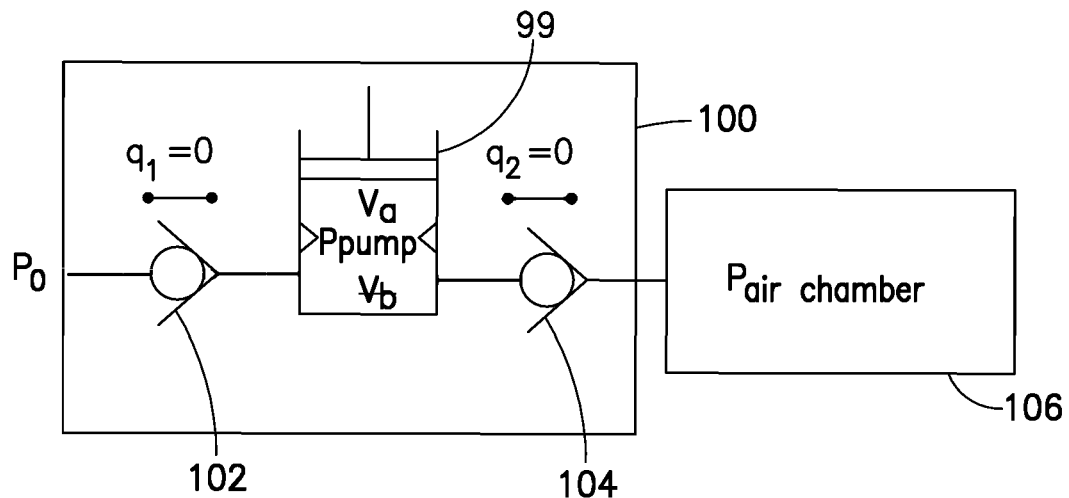
FIGS. 5(a)-(d) show schematic diagrams of a third improvement of the Odon device during use when applying positive pressure.
Figure 5B:
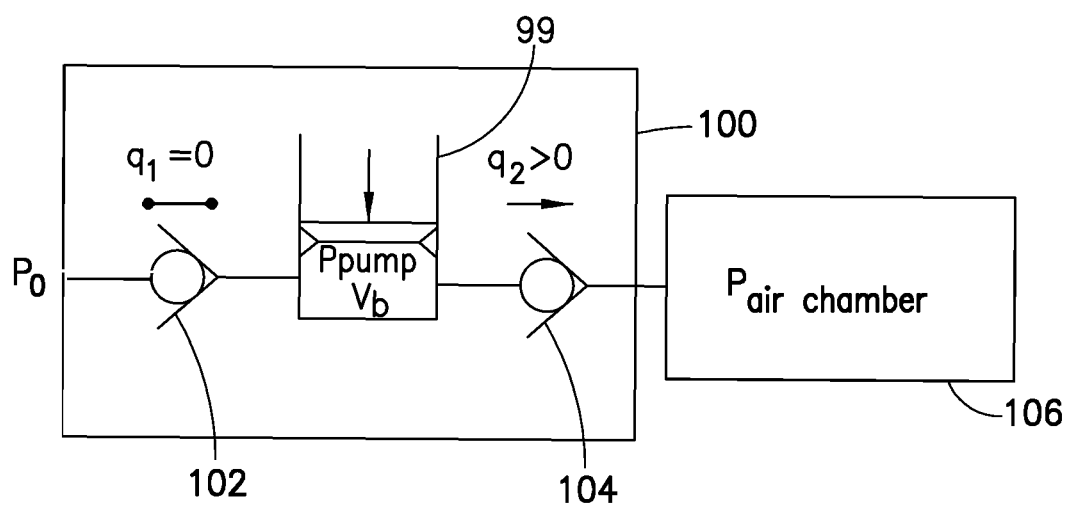
Figure 5C:
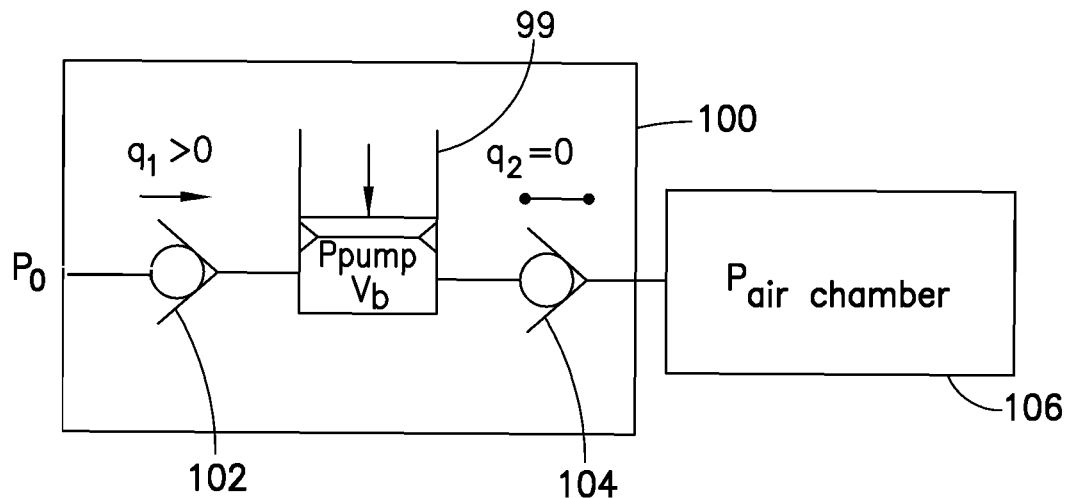
Figure 5D:
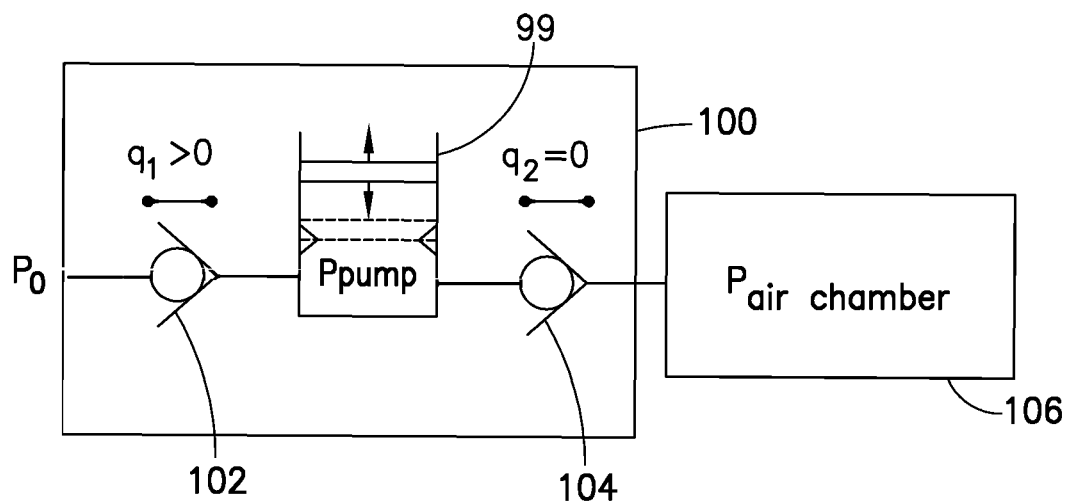

When steps depicted in FIGS. 5(b) and 5(c) are repeated (that is, repeated pump-release actions on the central chamber 99), a juncture will be reached whereby pressure equilibrium is reached, that is $P_{pump}=P_{chamber}$, and $q_1=q_2=0$ since there is no air flow between any of the central chamber 99, the air chamber 106 and the atmosphere.

The following paragraphs provide theoretical aspects in relation to the workings of the pressure limited pump 100. By controlling a ratio of compressible volume ($V_a$) and incompressible volume ($V_b$) in the central chamber 99, a maximum negative pressure that can be delivered by the central chamber 99 can be designed (defined) using Boyle's Law as follows: In FIG. 7(a), $P_{pump} V_b = P_0 (V_a+V_b)$ In FIG. 7(c), $P_{pump\ initial} V_b = P_{pump\ final} (V_a+V_b)$, so $P_{pump\ final} = P_{pump\ initial} \times [V_b/V_a+V_b]$.

Therefore, $P_{pump\ final} < P_{pump\ initial}$

Assuming $P_{chamber} = P_0$ at FIG. 7(b), $P_{pump\ final} < P_{chamber}$

Figure 7C:
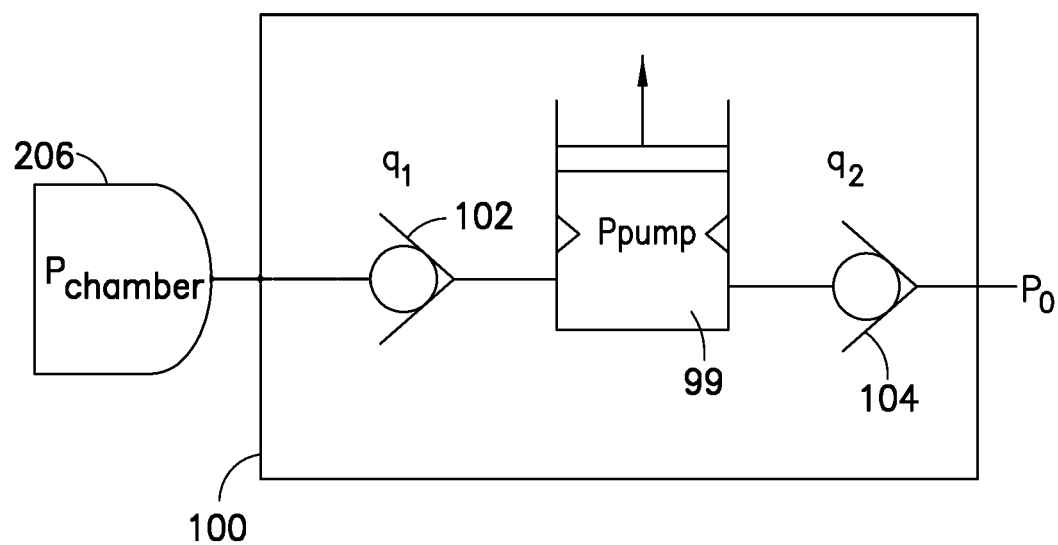

Repeating FIGS. 7(b) and 7(c) until $P_{pump\ final} = P_{chamber}$, this indicates that by managing $V_a$ and $V_b$, a pressure limit for $P_{chamber}$ can be obtained.

Based on the preceding paragraphs, it should be appreciated that the aforementioned first, second and third improvements to the apparatus 20 can be applied individually or in any combination when seeking to enhance the apparatus 20.

Whilst there have been described in the foregoing description preferred embodiments of the present invention, it will be understood by those skilled in the technology concerned that many variations or modifications in details of design or construction may be made without departing from the present invention.

The invention claimed is:

1. A method of using a pressure limitation apparatus configured to operate with a birth assistance device when attached via a conduit, the method comprising:

applying a positive pressure to thereby inflate an inflatable section of the birth assistance device, wherein the inflatable section is inflated by a pressure limited pump comprising a central chamber for receiving and containing a gas, a first check valve allowing air to pass therethrough and into the central chamber and preventing back flow of air out of the central chamber, a second check valve allowing air to pass therethrough and out of the central chamber and preventing back flow of air into the central chamber, the central chamber including a compressible portion having a compressible volume and an incompressible portion having an incompressible volume, wherein the compressible portion and the incompressible portion remain in fluid communication and wherein a ratio of the incompressible volume and the compressible volume defines a pressure of the air passing through the second check valve; and compressing the compressible portion of the central chamber such that air flows into the inflatable section of the birth assistance device.

* * * * *